United States Patent
Erdem et al.

(10) Patent No.: US 7,311,807 B2
(45) Date of Patent: Dec. 25, 2007

(54) PROCESS FOR THE SEPARATION OF MIXTURES CONTAINING M-AND P-DICHLOROBENZENE

(75) Inventors: Gültekin Erdem, Hamburg (DE); Morris Leckebusch, Wuppertal (DE); Günter Olf, Leverkusen (DE); Kay-Jochen Rinck, Bergisch Gladbach (DE); Günter Zühlke, Rösrath (DE)

(73) Assignee: Lanxess Deutschland GmbH, Leverkusen (DE)

( * ) Notice: Subject to any disclaimer, the term of this patent is extended or adjusted under 35 U.S.C. 154(b) by 232 days.

(21) Appl. No.: 10/701,339

(22) Filed: Nov. 4, 2003

(65) Prior Publication Data

US 2004/0144637 A1  Jul. 29, 2004

(30) Foreign Application Priority Data

Nov. 4, 2002  (DE)  ............................... 102 51 191

(51) Int. Cl.
*B01D 3/40* (2006.01)
*C07C 17/383* (2006.01)

(52) U.S. Cl. ............................. 203/48; 203/51; 203/57; 203/60; 203/99; 203/DIG. 19; 203/33; 570/178; 570/219

(58) Field of Classification Search ................ 203/33, 203/48, 51, 57, 60, 99, DIG. 19; 570/178, 570/219
See application file for complete search history.

(56) References Cited

U.S. PATENT DOCUMENTS

| | | | |
|---|---|---|---|
| 3,170,961 A | 2/1965 | Britton et al. | 260/650 |
| 3,800,002 A * | 3/1974 | Chikatsu et al. | 585/4 |
| 3,847,755 A | 11/1974 | Chanel et al. | 203/57 |
| 4,036,703 A | 7/1977 | Leroi et al. | 203/57 |
| 4,292,142 A * | 9/1981 | Berg | 203/51 |
| 4,300,004 A * | 11/1981 | Wissner et al. | 570/211 |
| 5,152,875 A | 10/1992 | Rittner et al. | 203/48 |
| 5,436,377 A * | 7/1995 | Pies et al. | 570/211 |
| 6,478,965 B1 * | 11/2002 | Holtzapple et al. | 210/634 |

FOREIGN PATENT DOCUMENTS

| | | |
|---|---|---|
| GB | 1 373 325 | 11/1974 |
| JP | 53 44528 | 4/1978 |
| JP | 54 160322 | 12/1979 |
| JP | 58 174333 | 10/1983 |
| JP | 62-123135 | 11/1985 |
| JP | 11 158093 | 6/1999 |

OTHER PUBLICATIONS

Database WPI, Section Ch, Week 198728, Derwent Publications Ltd., London, GB; Class E15, AN 1987-194650 XP002271964 & JP 62 123135 A (Sumitomo Chem IND KK) Jun. 4, 1987 "Zusammenfassung".

* cited by examiner

*Primary Examiner*—Virginia Manoharan
(74) *Attorney, Agent, or Firm*—Michael A. Miller

(57) ABSTRACT

A process for the separation of dichlorobenzene mixtures containing m- and p-dichlorobenzene in which:
  (i) the mixture is as an extracting agent contacted with a phosphoric ester of the general formula (I) as an extracting agent

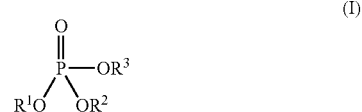

(I)

in which $R^1$, $R^2$ and $R^3$ are identical or different and represent an aliphatic or cycloaliphatic alkyl or alkenyl radical and $R^1$, $R^2$, and $R^3$ together contain at least 3C-atom and not more than 12 C-atoms, or a mixture of different Auxiliary phosphoric esters (I) of formula or is contacted with a phosphine oxide of the general formula (II) as an extracting agent

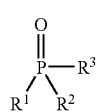

in which $R^1$, $R^2$ and $R^3$ are identical or different and represent an aliphatic or cycloaliphatic alkyl or alkenyl radical or hydrogen, and $R^1$, $R^2$ and $R^3$ together contain at least 3 C-atoms and not more than 12 C-atoms, or a mixture of different phosphine oxides of formula (II) or a mixture of said phosphoric esters of formula (I) and phosphine oxides of formula (II), and subsequently (ii) the components of the mixture are separated into a m-dichlorobenzene- and a p-dichlorobenzene-containing fraction, and finally (iii) the extracting agent is separated from one of the fractions obtained.

9 Claims, 1 Drawing Sheet

PROCESS FOR THE SEPARATION OF MIXTURES CONTAINING M-AND P-DICHLOROBENZENE

BACKGROUND OF THE INVENTION

1. Field of the Invention

The invention relates to a process for the separation of m-dichlorobenzene and p-dichlorobenzene by extractive rectification using extracting agents and separating off these extraction agents. More specifically, the invention relates to a process for preparing m-dichlorobenzene and p-dichlorobenzene in high purity from mixtures which contain m-dichlorobenzene and p-dichlorobenzene, as well as a process for using certain specified substances as extracting agents in said process.

2. Brief Description of the Prior Art

Pure dichlorobenzene, which are particularly useful as important intermediates for dyes, fragrances and pharmaceuticals and processes for preparing them are generally known in the art. The processes are, however, plagued with difficulties in effecting recovery of pure m-dichlorobenzene and pure p-dichlorobenzene.

In the conventional process for the preparation of dichlorobenzene by the chlorination of benzene, there are obtained chlorobenzene and more highly chlorinated benzenes (e.g. trichlorobenzenes) in addition to the three isomeric dichlorobenzene (DCB). While monochlorobenzene and the more highly chlorinated benzenes can be easily separated from the dichlorobenzene by distillation, the recovery of pure m-dichlorobenzene and pure p-dichlorobenzene is among the most difficult separation tasks of aromatic intermediate chemistry. This is because the boiling points of m- and p-DCB differ by less than 1° C., so that the distillative separation in high purity by fractional rectification is virtually impossible.

The following are illustrative examples of the prior art processes for the separation, and the problems associated therewith. Owing to the difficulty in separation of m-dichlorobenzene and p-dichlorobenzene, the prior art approaches for obtaining the isomers in pure form is via complicated chemical detours. Thus, for example in JP 53044528, the m-dichlorobenzene and the o-dichlorobenzene in a dichlorobenzene mixture are selectively sulphonated with the aid of sulphuric acid. After unreacted p-dichlorobenzene has been separated off, m-dichlorobenzene and o-dichlorobenzene are obtained by desulphonation at higher temperature. U.S. Pat. No. 3,170,961 proposes separation via bromine isomers. In this process, the dichlorobenzene are brominated, and the resulting bromine isomers are separated by distillation in order to obtain pure dichlorobenzene by elimination of bromine. As would be realized, these processes are difficult and expensive.

The separation of mixtures of m-dichlorobenzene and p-dichlorobenzene into pure m-dichlorobenzene and pure p-dichlorobenzene by melt crystallization is not possible because the binary system has a eutectic point at a content of 88% by weight for m-dichlorobenzene. Hence, only one of the two isomers can be obtained in pure form. Moreover, low temperatures (about −30° C.) required for the isolation of m-dichlorobenzene, makes the process uneconomical.

The literature describes other processes for the separation of m-dichlorobenzene and p-dichlorobenzene, which processes are based on the different adsorption on zeolites. JP 11 158 093, for example, mentions separation factors between m-DCB and p-DCB which all technically lead to pure isomers. However, these processes have the disadvantage that the regeneration of the zeolite is complicated and large amounts of solvents have to be circulated.

Of particular interest here is a separation technique comprising extractive rectification. For this technique, there is added to the mixture to be separated an extracting agent which influences the vapour-liquid phase equilibrium via selective interaction in such a manner that separation factors are not equal to one. JP 58 174 333 mentions aniline derivatives as extractive agents. According to this technique, separation factors in the range from 1.08 to 1.16 are obtained. The class of extracting agents mentioned by this patent includes substances which have an unfavourable boiling point, and others which are technically difficult to prepare and are therefore expensive. JP 54 160 322 mentions sulpholane (separation factor 1.15), decanol (separation factor 1.1) and the three isomers of cresol (separation factors 1.07 to 1.14). Owing to its high boiling point and its chemical instability at relatively high temperatures, sulpholane is not suitable for the separation of DCB isomers. In a dissertation (Unverdorben, L., University of Erlangen-Nürnberg, 1992), the separation factors of alkenyl carbonates (ethylene carbonate, propylene carbonate) were determined to be 1.13 to 1.14.

The disadvantages of the abovementioned substances can be summarized as follows. Some of the substances having separation factors of <1.15 require very high separation efficiency; some of the substances are known to be toxic, and some of the substances have boiling points which are so unfavourable that the separation between extracting agent and p-DCB is complicated, and some of the substances exhibit decomposition and as such cannot be used repeatedly.

SUMMARY OF THE INVENTION

It was, therefore, the object of this invention to develop a process based on extractive rectification, by means of which m-DCB and p-DCB can be separated from mixtures which contain m-DCB and p-DCB. The extracting agents required for this purpose should produce separation factors (m-DCB/p-DCB) substantially differing from one, so that the separation effort is reduced. The extracting agent should in particular have a higher boiling point than the isomer pair m-DCB and p-DCB to be separated. Furthermore, the boiling point difference at 1 atm. between the extracting agent and p-DCB should as far as possible be at least 20° C., preferably at least 35° C., in order to permit simple separation of the extracting agent from the p-DCB by distillation. The extracting agents should moreover be toxicologically and ecologically safe.

This object is achieved, according to the invention, by using selected phosphoric esters, e.g. triethyl phosphate, and phosphine oxides, e.g. tri-n-propylphosphine oxide or tri-n-butylphosphine oxide, or mixtures thereof as extracting agents in the process.

Accordingly, the invention relates to a process for the separation of dichlorobenzene mixtures containing m- and p-dichlorobenzene by extractive rectification using an extracting agent, separation of the components into an m-dichlorobenzene- and p-dichlorobenzene-containing fraction and final separation of the extracting agent from one of the fractions obtained, characterized in that the extracting agent used is a phosphoric ester of the general formula (I)

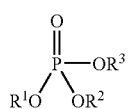

(I)

in which R¹, R² and R³ are identical or different and represent an aliphatic or cycloaliphatic alkyl or alkenyl radical and R¹, R² and R³ together contain at least 3 and not more than 12 C atoms, or a mixture of different phosphoric esters of this type or a phosphine oxide of the general formula (II)

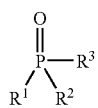

(II)

in which R¹, R² and R³ are identical or different and represent an aliphatic or cycloaliphatic alkyl or alkenyl radical or hydrogen, and R¹, R² and R³ together contain at least 3 and not more than 12 C atoms, or a mixture of different phosphine oxides of this type or a mixture of said phosphoric esters and phosphine oxides.

DETAILED DESCRIPTION OF THE INVENTION

Figure 1:
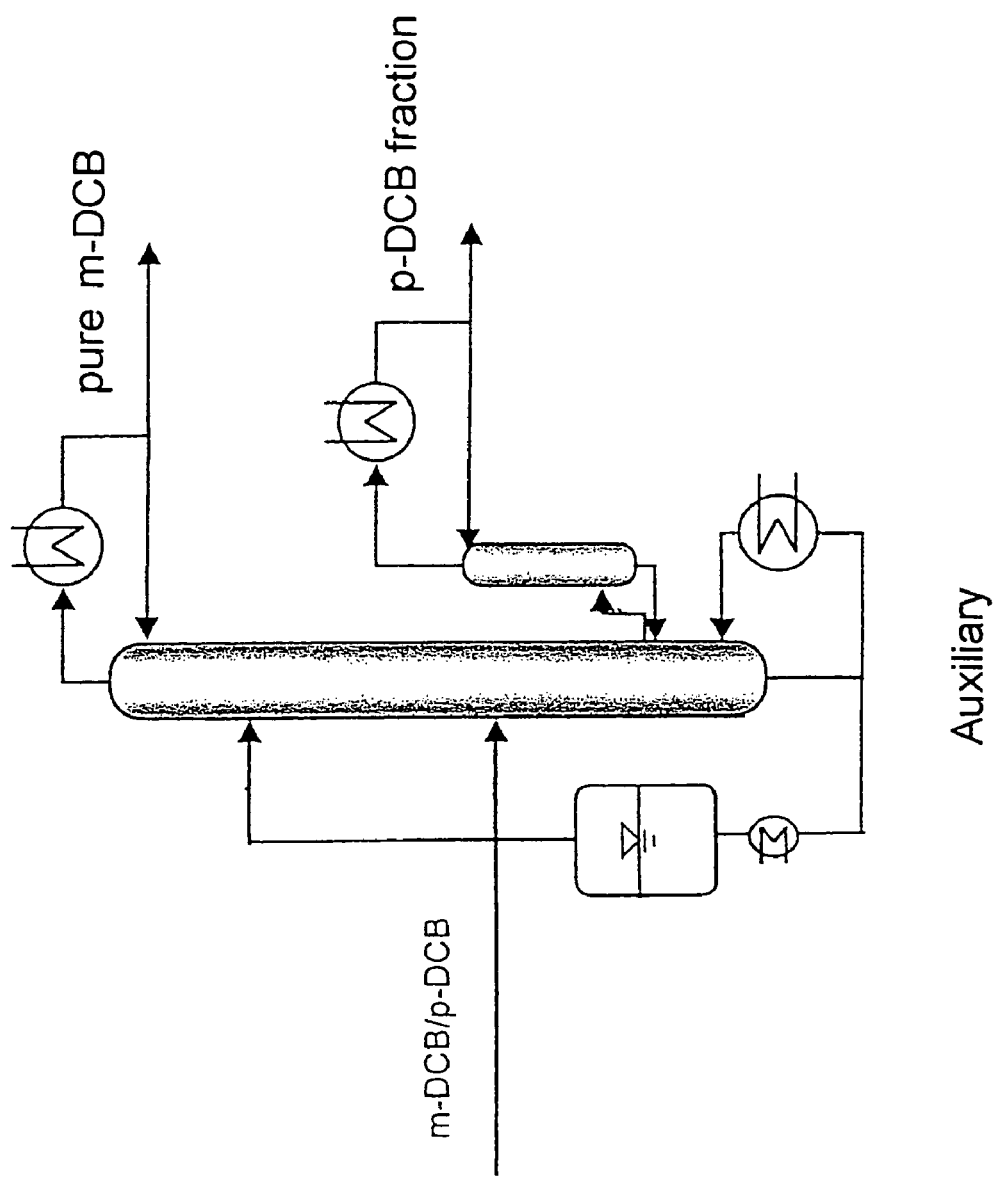
FIG. 1 shows a rectification column for carrying out the separation of p-DCB and m-DCB, in accordance with the invention.

The invention is described more fully hereunder with particular reference but without limitation to its preferred embodiments. The abovementioned alkane radicals and alkene radicals can preferably be straight-chain, branched, cyclic, saturated and unsaturated.

In the formula (I) or (II) representing the extracting agent, R¹, R² and R³ are preferably identical or different and represent a radical from the series: methyl, ethyl, n-propyl, isopropyl, n-butyl, tert-butyl, n-pentyl, sec-butyl.

Particularly preferred extracting agents are triethyl phosphate, tripropylphosphine oxide or tributylphosphine oxide, alone or as a mixture.

In a preferred process, the separation is carried out in a rectification column, with the pressure at the top of the column being in the range from 5 to 100 hPa and the pressure difference between the bottom of the column and the top of the column being 0 to 100 hPa, and optionally the number of theoretical plates being 20 to 200.

More preferably, the pressure at the top of the column is 5 to 30 hPa and the pressure difference between the bottom of the column and the top of the column is 0 to 20 hPa, and optionally the number of theoretical plates is 60 to 120.

Also, in a preferred embodiment of the process, the weight ratio of feed of the extracting agent to feed of the m-/p-dichlorobenzene mixture is in particular 2:1 to 40:1, particularly preferably 6:1 to 12:1. In a preferred embodiment of the process, the weight ratio of reflux to distillate is 1:1 to 20:1, particularly preferably 3:1 to 8:1.

The invention also relates to the use of phosphoric esters and phosphine oxides, in particular those of the formulae (I) or (II), as extracting agents for the extractive rectification.

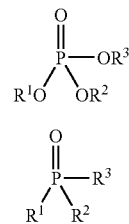

The radicals R¹, R² and R³ have the abovementioned meaning.

In accordance with the invention, one can obtain m-DCB fractions and p-DCB fractions which virtually no longer contain the other isomer from mixtures which contain m-DCB and p-DCB by extractive rectification. The mixture used may contain more m-DCB than p-DCB or vice versa. The mixture used may also contain the two isomers in equal concentration. High purities of virtually 100% can be achieved for the total concentration range. In addition to these two DCB isomers, the isomer mixture may also contain further chlorinated benzenes, such as, for example, monochlorobenzene, o-dichlorobenzene and more highly chlorinated aromatics. Furthermore, substances which are usually present in the chlorination of benzene or are formed in the reaction, such as, for example, chlorinated nitrochlorobenzenes, benzene, hydrogen chloride and catalysts, may be present.

To demonstrate the efficiency of the extracting agents used according to the invention, the separation factors are listed in the table below. With the exception of the data on tributylphosphine oxide, these values were measured at 120° C. by the headspace method, which is explained in Verfahrenstechnik 8 (1974) No.12, pages 343-347. The measurements were carried out at a concentration in the liquid of 10 mol % of m-DCB, 10 mol % of p-DCB and 80 mol % of extracting agent. The data on tributylphosphine oxide were measured using a dynamic equilibrium apparatus at 80 hPa and were converted by means of classical thermodynamics to 120° C. and 10 mol % of m-DCB, 10 mol % of p-DCB and 80 mol % of tri-n-butylphosphine oxide. For comparison of the efficiency of these extracting agents, the corresponding measured values for sulpholane and propylene carbonate have also been included in the table. The value for propylene carbonate is a measured value from Unverdorben, L., Dissertation, University of Erlangen-Nürnberg, 1992.

TABLE

| Extracting agent | Separation factor |
| --- | --- |
| Triethyl phosphate | 1.23 |
| Tri-n-propylphosphine oxide | 1.21 |
| Tri-n-butylphosphine oxide | 1.17 |
| Sulpholane | 1.14 |
| Propylene carbonate | 1.14 |

The tests showed that the phosphoric esters and the phosphine oxides have very good separation factors compared with the other substances. Long-term stability investigations on phosphoric esters/dichlorobenzene mixtures show that only very small amounts of ester have been eliminated by reaction even after weeks. The phosphine oxides likewise have a high thermal stability. Furthermore, both classes of substances exhibit no reactions with chlorinated aromatics under the relevant conditions. From the foregoing positive material properties easy separability from the dichlorobenzene, it would be realized that phosphoric esters and phosphine oxides are outstandingly suitable as extracting agents for an extractive rectification of m-/p-DCB mixtures.

In general, the mixture fed into the extraction column and to be separated has a temperature which is between 20 and 80° C. and preferably between 40 and 60° C., depending on the chosen column pressure. The feed temperature of the extracting agent is typically between 50 and 70° C. The bottom temperature in the extractive rectification column should expediently not exceed 180° C., preferably 130° C.

The process according to the invention can also be used for obtaining pure p-DCB from a mixture of m-DCB and p-DCB or for obtaining both pure m-DCB and pure p-DCB from a mixture of m-DCB and p-DCB. The extractive rectification process permits applications for the separation of m-DCB and p-DCB in which the extractive rectification is combined with a melt crystallization or a chromatography in order to obtain very high purities.

The process permits in particular applications for the separation of m-DCB and p-DCB in which both the extractive rectification of m-DCB and p-DCB and the joint separation of the p-DCB and of the remaining m-DCB from the extracting agent are effected in a single column with vapour side-stream take-off. In this case, the column preferably has a multistage column rectification section (side-stream column) connected to the vapour side-stream take-off, with top condenser and reflux divider, in which section the p-DCB and the remaining m-DCB are separated from the extracting agent. The pure m-DCB is obtained at the top of the column and the pure extracting agent in the bottom, which extracting agent is recycled into the column (FIG. 1). The quality of the top product here is ensured by means of suitable methods, for example by a product analysis or an online analysis, which correspondingly influences the reflux ratio in the column. The side-stream take-off rate is regulated, for example, via a temperature measurement at an appropriately sensitive point in the side-stream column operated with constant reflux ratio, which temperature measurement regulates the degree of opening of a valve in the condensate line downstream of the top condenser of the side-stream column. Owing to the associated influence on the liquid level and hence on the effective area in this condenser, automatic regulation of the TEP concentration in the side-stream removed is effected.

The separation of m- and p-dichlorobenzene and the recovery of the extracting agent are preferably carried out in a rectification column, a side-stream column being connected to the rectification column via a vapour side-stream take-off for recovery of the extracting agent.

The process permits in particular applications in which the extracting agent is separated from the p-dichlorobenzene by distillation or by extraction or by crystallization.

A particularly advantageous variant of the process is one in which the extractive rectification is located downstream of a melt crystallization, in order to obtain the desired isomer, in particular p-dichlorobenzene, in very high purity (>99% by weight) with reduced energy consumption.

The invention is further illustrated but is not intended to be limited by the following examples in which all parts and percentages are by weight unless otherwise specified.

EXAMPLES

A laboratory column which has an internal diameter of 30 mm, has an externally heated vacuum jacket provided with an internal reflective coating, is packed with 3 mm×3 mm (mesh size) mesh rings and has an effective separation height of 2.5 m is fed at a height of 1.0 m with the mixture to be separated and consisting of 75% by weight of m-DCB and 25% by weight of p-DCB at a temperature of 50° C. and at a height of 2.0 m with the extracting agent triethyl phosphate at a temperature of 60° C.

The pressure at the top of the column is 10 hPa and that at the bottom of the column is 30 hPa. The extracting agent leaves the bottom of the column as a boiling liquid. Furthermore, the bottom stream contains less than half the m-DCB used and more than 99.5% of the p-DCB used. The m-DCB condensed in the condenser and containing less than 1% by weight of p-DCB is taken off at the top of the column. The amount of distillate to be taken off and comprising highly pure m-DCB is set at 25 g/h and the reflux ratio (amount of reflux/distillate) is set at 5, while 60 g/h of mixture to be separated and 500 g/h of triethyl phosphate are fed into the column.

In a second column, which likewise has an internal diameter of 30 mm and an externally heated vacuum jacket provided with an internal reflective coating is packed with 3 mm×3 mm mesh rings, the p-DCB obtained in the bottom of the extractive rectification column and the remaining m-DCB are separated together from the extracting agent. The effective separation height of this second column is likewise 2.5 m. The column is fed at a height of 1.5 m with the feed mixture comprising p-DCB, remaining m-DCB and extracting agent, which was cooled beforehand in a cooler to 65° C.

In the second column, the top pressure is likewise 10 hPa and the bottom pressure likewise 30 hPa. The extracting agent leaves the bottom of the column as a boiling liquid in pure state, while the mixture comprising p-DCB and remaining m-DCB and condensed in the condenser is taken off at the top of the column. The reflux ratio in this column is set to 2. The pure extracting agent obtained in the bottom is cooled to 65° C. in a downstream cooler and fed into a 5 litre buffer vessel.

The extracting agent flowing into the extractive rectification column is fed from this buffer vessel, so that a closed extracting agent circulation is present.

By means of the experiment described, a mixture of 75% by weight of m-DCB and 25% by weight of p-DCB was separated to a distillate comprising >99% by weight of m-DCB and into a discharge enriched with p-DCB.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the separation of dichlorobenzene mixtures containing m- and p-dichlorobenzene by extractive rectification wherein:

(I) the mixture is contacted either with one phosphoric ester of the general formula (I) as an extracting agent

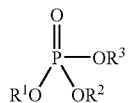

wherein $R^1$, $R^2$ and $R^3$ are identical or different and are selected from the group consisting of aliphatic or cycloaliphatic alkyl or alkenyl radical wherein $R^1$, $R^2$ and $R^3$ together contain at least 3 C-atoms and not more than 12 C-atoms, or a mixture of phosphoric esters of formula (I) or is contacted with one phosphine oxide of the general formula (II) as an extracting agent

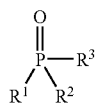

in which $R^1$, $R^2$ and $R^3$ are identical or different and are selected from the group consisting of aliphatic or cycloaliphatic alkyl or alkenyl radical or hydrogen, wherein $R^1$, $R^2$ and $R^3$ together contain at least 3 C-atoms and not more than 12 C-atoms, or a mixture of phosphine oxides of formula (II) or a mixture of phosphoric esters of formula (I) and phosphine oxides of formula (II), and subsequently
  (ii) the components of the mixture are separated into a m-dichlorobenzene- and a p-dichlorobenzene-containing fraction, and finally
  (iii) the extracting agent is separated from one of the fractions obtained.

2. Process according to claim 1, wherein the formula (I) or (II) for the extracting agent, $R^1$, $R^2$ and $R^3$ are identical or different and represent a radical selected from the group consisting of methyl, ethyl, n-propyl, isopropyl, n-butyl, tert-butyl, n-pentyl, and sec-butyl.

3. Process according to claim 1, wherein the extracting agent is triethyl phosphate, tripropylphosphine oxide, tributylphosphine oxide alone or as a mixture.

4. Process according to claim 1, wherein the separation is carried out in a rectification column, wherein pressure at the top of the column is in the range of 5 to 100 hPa and pressure difference between the bottom of the column and the top of the column being 0 to 100 hPa and optionally the number of theoretical plates being 20 to 200.

5. Process according to claim 4, wherein the pressure at the top of the column is 5 to 30 hPa and the pressure difference between the bottom of the column and the top of the column is 0 to 20 hPa and optionally the number of theoretical plates is 60 to 120.

6. Process according to claim 1, wherein a weight ratio of mass flow of reflux to distillate is 1:1 to 20:1.

7. Process according to claim 1, wherein a weight ratio mass flow of feed of the extracting agent to feed of the m-dichlorobenzene and p-dichlorobenzene mixture is 2:1 to 40:1.

8. Process according to claim 1, wherein the separation of m- and p-dichlorobenzene and the separation of the extracting agent is carried out in a rectification column, with a side-stream column being connected to the rectification column via a vapor side-stream take-off for recovery of the extracting agent.

9. Process according to claim 1, wherein a melt crystallization of the m-dichlorobenzene or p-dichlorobenzene, is provided downstream of the extractive rectification.

* * * * *